US00PP29972P2

(12) United States Plant Patent
Hansen

(10) Patent No.: US PP29,972 P2
(45) Date of Patent: Dec. 11, 2018

(54) ***DIANTHUS* PLANT NAMED 'DOUBLE BUBBLE'**

(50) Latin Name: *Dianthus* hybrid
Varietal Denomination: Double Bubble

(71) Applicant: Hans A Hansen, Zeeland, MI (US)

(72) Inventor: Hans A Hansen, Zeeland, MI (US)

(73) Assignee: Walters Gardens Inc, Zeeland, MI (US)

( * ) Notice: Subject to any disclaimer, the term of this patent is extended or adjusted under 35 U.S.C. 154(b) by 0 days.

(21) Appl. No.: 15/932,097

(22) Filed: Feb. 1, 2018

(51) Int. Cl.
*A01H 5/02* (2018.01)

(52) U.S. Cl.
USPC ..... Plt./281
CPC ..... *A01H 5/02* (2013.01)

(58) Field of Classification Search
USPC ..... Plt./281, 277
CPC ..... A01H 5/02
See application file for complete search history.

*Primary Examiner* — Kent L Bell

(57) ABSTRACT

A new and unique plant cultivar of perennial carnation or pinks, *Dianthus* plant named 'Double Bubble' with numerous, small, fully-double, lightly-fragrant flowers producing a rounded full face. Medium pink petals with lighter pink toward apex are irregularly and finely toothed on the distal margin. Heavily branched stems cover the top of the plant with flowers for about six weeks. The habit is compact with long, thin, blue-green foliage.

1 Drawing Sheet

Botanical denomination: *Dianthus* hybrid.
Cultivar designation: 'Double Bubble'.

BACKGROUND OF THE INVENTION

The present invention relates to the new and distinct cultivar of carnation or pinks from the genus *Dianthus* and given the cultivar name 'Double Bubble'. The new plant was the result of an intentional cross on May 14, 2012 under the direction of the inventor between *Dianthus* x *allwoodii* 'Frosty Fire' (not patented) as the female or seed parent and 'Valda Isolde' U.S. Plant Pat. No. 13,915 (known by the tradename Fancy Knickers) as the male or pollen parent. The cross was harvested and sown on Jul. 2, 2012. The new hybrid was first isolated from trials at a wholesale perennial nursery in Zeeland, Mich. during the summer of 2013 as a single seedling clone and given the breeder number 12-65-2 later in the evaluation processes. *Dianthus* 'Double Bubble' has been asexually propagated at the same nursery in Zeeland, Mich. since 2013 using traditional shoot tip cutting procedures and found to reproduce plants that are identical and exhibit all the characteristics of the original plant.

No plants of *Dianthus* 'Double Bubble' have been sold in this country, or anywhere in the world, under this or any name or tradename, prior to the filing of this application, nor has any disclosure of the new plant been made prior to the filing of this application with the exception of that which was disclosed or sold within one year of the filing of this application and was either derived directly or indirectly from the inventor.

SUMMARY OF THE INVENTION

*Dianthus* 'Double Bubble' has not been evaluated under all possible environmental conditions. The phenotype may vary with variations in environment including: growing temperature, available sunlight, nutrients, water, etc. without a change in the genotype of the plant.

Compared with the new plant, the female parent 'Frosty Fire' has typically five petals on smaller, single, red flowers without bar or band, and the habit is about one-third smaller in height compared to the pink double flowers and taller 'Double Bubble'. The male parent, 'Fancy Knickers', has white flower petals with a magenta base compared with the pink-colored petals without markings or lighter margins. The nearest comparison cultivar known to the inventor is 'Sweetie Pie' U.S. Plant Pat. No. 27,989 which differs from the new plant by having fewer petals per flower, and petals with lighter pink hue and a darker pink eye or band. 'Holkahoripink' U.S. Plant Pat. No. 28,557 is a shorter plant that produces single flowers with five petals and the coloration is of a darker more purple hue.

*Dianthus* 'Double Bubble' is distinct from its parents and all other *Dianthus* known to the applicant in the following combined traits:

1. Fully-double flowers opening up with petal counts per flower averaging about 38 petals per flower.
2. Petals having a medium pink coloration with slightly lighter pink toward apex;
3. Petal margin irregularly and finely toothed.
4. Typically two flowers per stiff, upright peduncle.
5. Flowers producing a lightly-sweet spicy fragrance.
6. Flower near top of clump, vigorous, with compact heavily-branched habit and finely-textured blue-green foliage.

BRIEF DESCRIPTION OF THE DRAWINGS

The photographs of the new invention are of a two-year-old plant grown in full-sun trial garden and demonstrate the overall appearance of the plant including the unique traits. The colors are as accurate as reasonably possible with color reproductions. Some slight variation of color may occur as a result of lighting quality, intensity, wavelength, direction or reflection.

DETAILED DESCRIPTION OF THE PLANT

Figure 1:
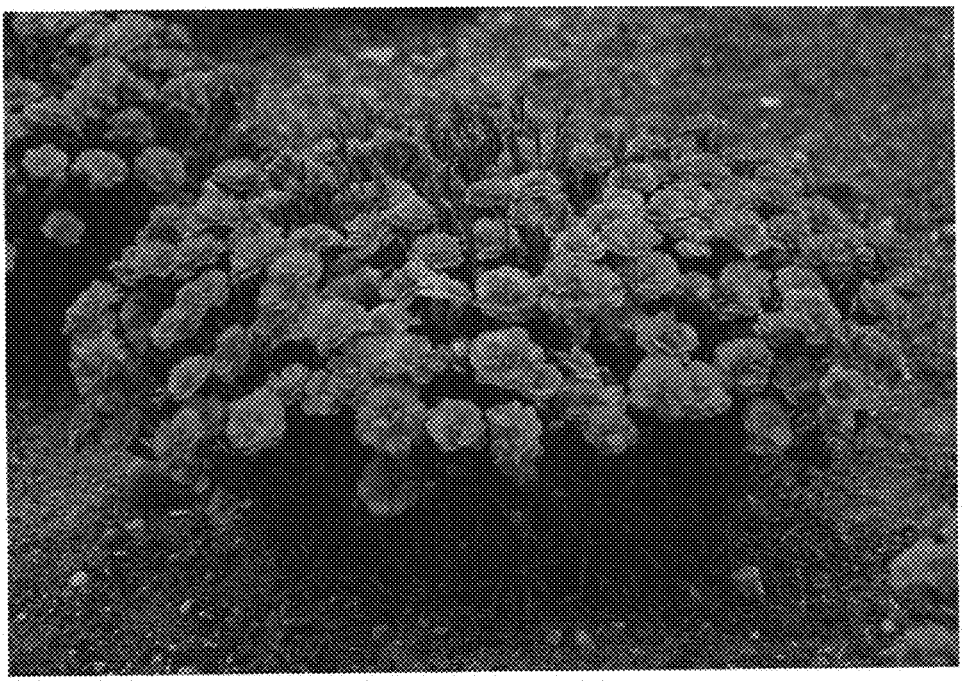
FIG. 1 shows the habit of the plant in mid-season flowering.
Figure 2:
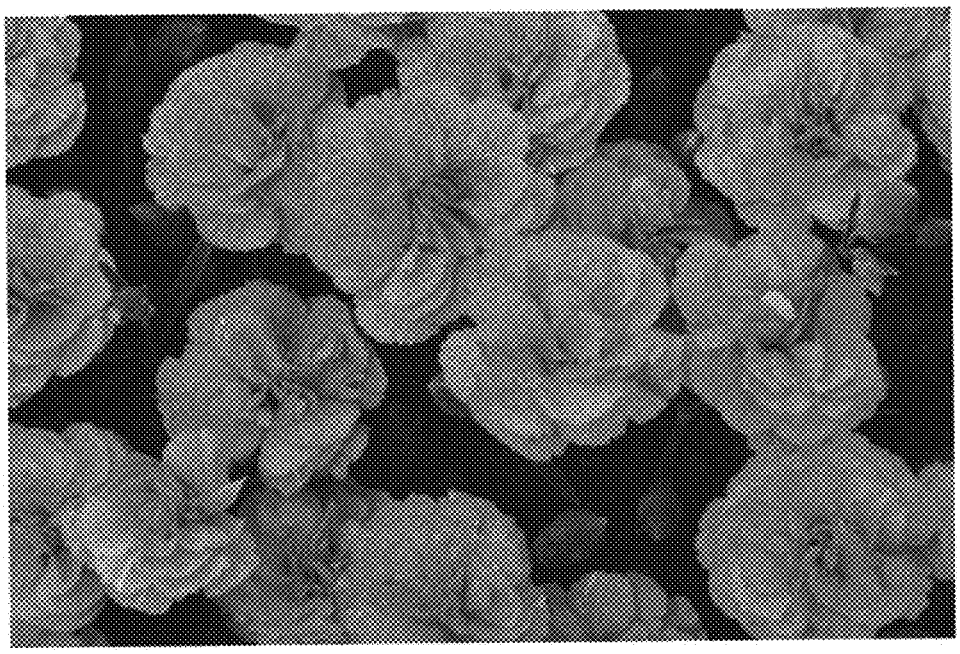
FIG. 2 shows a close-up of the flowers and bud.

The following detailed description of the new plant is based on observations of two-year-old plants in greenhouse-grown containers in addition to two-year-old plants in full-sun trial garden at a nursery in Zeeland, Mich. with supplemental watering, light additions of fertilizer and free of other plant growth regulators. All color usage is in accordance with the 2015 edition of The Royal Horticultural Colour Chart except where common dictionary terms are used.

Botanical classification: *Dianthus* hybrid;

Parentage: *Dianthus* x *allwoodii* 'Frosty Fire' as the female or seed parent and *Dianthus* 'Fancy Knickers' as the male or pollen parent;

Plant habit: Caespitose, herbaceous, evergreen, winter-hardy perennial; stems and peduncles branched, mostly erect stems; height of foliage about 10.0 cm and about 30.0 cm across; height in flower is about 28.0 cm;

*Root system*.—Fine, fibrous; color nearest RHS 155D.

*Vigor*.—Good, spring planted plugs finish in 3.8 liter pots in seven to eight weeks.

Foliage:

*Leaf type*.—Simple, linear, opposite, decussate, sessile, glabrous, glaucous both adaxial and abaxial; margin entire to microscopically serrulate; acute apex; base decurrent; no fragrance detected.

*Leaf dimensions*.—To about 5.3 cm long and about 3.5 mm wide, average about 4.3 cm long and 2.5 mm wide.

*Leaf color*.—Young expanding leaves abaxial nearest RHS N138B and adaxial nearest RHS N138B; mature abaxial nearest RHS N138B and adaxial nearest RHS 137A.

*Venation*.—Not pronounced; obscurely pinnate, coloration same as that of leaf top and bottom.

Stems: About 24 per plant; upright; terete, glabrous, glaucous; solid; branching in upper nodes;

*Stem size*.—Total including peduncle about 24.0 cm long and 8.0 cm below peduncle, about 2.5 mm diameter at base.

*Stem color*.—Nearest RHS N138A.

*Branching*.—Heavily branched; typically alternate from lower nodes; about 8 per main stem and about 200 per plant; branch size average about 14.0 cm long and 2.0 mm diameter at time of initial flowering.

*Nodes*.—To about 4.5 mm across; color nearest RHS 145D.

*Internodes*.—About 8 per stem before peduncle; average about 2.3 cm apart depending on growing temperature, shorter in cooler conditions.

Inflorescence:

*Type*.—Terminal, cymose; perfect; salverform; actinomophic; fully double.

*Attitude*.—Mostly upright to slightly outward around perimeter of plant.

*Dimension*.—About 3.2 cm across and extending about 3.4 cm above base of calyx tube and 1.2 cm wide at apex of calyces.

*Flower number*.—Up to 2 per stem; about 380 per plant.

*Pedicel*.—Glaucous, glabrous, terete, stiff; primarily upright.

*Pedicel size*.—On terminal flower average about 1.40 cm long and about 2.5 mm diameter; other flowers average about 4.5 cm long and 2.0 mm diameter.

*Pedicel color*.—Nearest RHS N138A.

*Flower bud*.—Slowly opening; glabrous; glaucous; with calyx still closed: tubular, oblong ovoid; about 2.0 cm long and 7.0 mm across at distal fusion point of sepals; with petals extended beyond calyx and still parallel to calyx side: terete, with rounded base and truncate apex or petal tops, about 2.6 cm long and 8.0 mm across at exposed petals.

*Flower bud color*.—With petals enclosed in calyx distally proximally between RHS 144B and RHS 145A and distally blend between RHS 137B and RHS 144A; with petals extended beyond calyx petal portion nearest RHS 73B.

*Flower period*.—Beginning late spring and continuing for about four weeks.

*Flower fragrance*.—Light, sweet spicy, clove-like.

*Flower lasting quality*.—Individually about 6 to 8 days on or cut from plant.

*Petals*.—Glabrous abaxial and adaxial; up to about 43 per flower, average about 40 in terminal flowers and average 27 in axillary flowers; consisting of a rounded blade or limb and a claw; limb and claw combined are flabellate; limb apex and distal margin crenate with irregular dentations average 1.0 mm wide and 1.0 mm long, basal limb and claw entire; folded backward between limb and claw to nearly a 90 degree angle; persistent.

*Petal dimensions*.—Whole petal to about 34.0 mm long and 20.0 mm across at limb, average about 28.0 mm long and about 18.0 mm wide at limb; claw tapering to attenuate base of about 1.0 mm across.

*Petal color*.—Young abaxial claw nearest RHS 145C, young abaxial limb base blend between RHS 75B and RHS 73B; young adaxial claw nearest RHS 145C, young adaxial limb base center nearest RHS 71B, young adaxial limb perimeter and basal perimeter between RHS 73A and RHS 68B; mature abaxial claw nearest RHS 145C, mature abaxial limb base thin bar about 1.5 mm wide nearest RHS 72A adaxial perimeter blend between RHS 73A and RHS 68B.

*Calyx*.—Glabrous, glaucous abaxial and adaxial; margins entire; consisting of five sepals with acute apex and fused base forming five-toothed campanulate corolla tube fused in about proximal 14.0 mm; campanulate to about 22.0 mm long and about 8.5 mm in diameter at apex.

*Sepals*.—Five; individually about 22.0 mm long and about 4.0 mm across at distal fusion.

*Sepal color*.—Abaxial base between RHS 144A and RHS 165B, distal base between RHS 137B and RHS 145A; abaxial base blend between RHS 144B and RHS 145A, distal portion blend between RHS 137A and RHS 144A; adaxial base nearest RHS 146D and distally nearest RHS 146B.

*Peduncle*.—Glabrous, glaucous, terete, stiff; about 16.0 cm long and about 3.0 mm diameter at base; attitude mostly upright.

*Peduncle color*.—Nearest RHS N138A.

*Epicalyx*.—Two sets of two subtending each flower adpressed to calyces; glaucous, glabrous both adaxial and abaxial; sessile; margin entire; outer set ovate with broadly acute apex and cuneate base, about 8.0 mm long and about 4.0 mm wide; inner set ovate with acute apex and truncate base, about 7.0 mm long and about 4.0 mm across.

*Epicalyx*.—Both sets abaxial base between RHS 144B and RHS 145A and distal portion blend between RHS 137B and RHS 144A; both sets adaxial base nearest RHS 146D and distal portion nearest RHS 146B; both sets distal margin about 1.0 mm to 2.0 mm wide transparent.

*Androecium*.—Up to 10; not well developed when present. Filaments: to 16.0 mm long and 0.3 mm diameter, average about 12.0 mm long and 0.3 mm diameter; color nearest RHS NN155D. Anthers: typically rudimentary; when present dorsifixed; to 2.0 mm long and 0.5 mm across; color nearest RHS 155D. Pollen: not observed.

*Gynoecium*.—Two or three; to 3.4 cm long. Pistil: two to three; to about 28.0 mm long. Style: rarely bifurcate, or commonly trifurcate just above ovary; puberulent adaxial; to 21.0 mm long and 1.5 mm across; color nearest RHS NN155D. Stigma: puberulent adaxial surface, curled around 360 degrees in distal 3.0 to 4.0 mm; about 7.0 mm long and 1.5 mm wide; color nearest RHS NN155D with faint blush of lighter than RHS 75D. Ovary: superior; ellipsoid-shaped, acute apex and truncate base; about 6.5 mm long and 4.0 mm diameter; color between RHS 144A and RHS 145A.

Fruit: Not observed;

Disease resistance: The new plant is resistance to center die out from fungus or high temperatures. The plant grows best with adequate moisture and well-drained soil, but is able to tolerate some drought once established. Hardiness at least from USDA zone 4 through zone 9.

It is claimed:

1. A new and distinct *Dianthus* plant named 'Double Bubble' essentially as herein described and illustrated.

* * * * *